(12) United States Patent
Nakamura (10) Patent No.: US 6,962,565 B2
(45) Date of Patent: Nov. 8, 2005

(54) EXCITATION LIGHT ILLUMINATING PROBE, VIDEO ENDOSCOPE SYSTEM, AND VIDEO ENDOSCOPE FOR FLUORESCENCE OBSERVATION

(75) Inventor: Tetsuya Nakamura, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 202 days.

(21) Appl. No.: 10/316,862

(22) Filed: Dec. 12, 2002

(65) Prior Publication Data

US 2003/0120129 A1 Jun. 26, 2003

(30) Foreign Application Priority Data

Dec. 26, 2001 (JP) .............................. 2001-393815

(51) Int. Cl.$^7$ .............................. A61B 1/06; A61B 6/00
(52) U.S. Cl. ...................... 600/179; 600/178; 600/160; 600/476
(58) Field of Search ................................ 600/160, 178, 600/179, 476, 478, 177; 362/187, 189, 551, 362/556, 278, 285

(56) References Cited

U.S. PATENT DOCUMENTS 3,103,723 A * 9/1963 Becker ........................ 24/3.12
3,737,722 A * 6/1973 Scharlack ............... 315/209 R
4,282,681 A * 8/1981 McCaslin ................... 446/484

(Continued)

FOREIGN PATENT DOCUMENTS

JP 11267099 10/1999

Primary Examiner—John P. Leubecker
(74) Attorney, Agent, or Firm—Greenblum & Bernstein, P.L.C.

(57) ABSTRACT

A video endoscope system for fluorescence observation includes a video endoscope, an illumination probe, a power supply unit, a signal processing unit and a display. The video endoscope has a part configured to be inserted in a body cavity, an objective optical system that forms an image of a subject based on a visible component of the light emitted through the distal end of the insert part, and a cut filter that filters out from the light incident onto the objective optical system, a component of light having a predetermined wavelength. An image pickup device picks up an image of the subject formed by the objective optical system to output an image signal. A light emitting device is provided to emit excitation light having a wavelength so as to excite tissue of a living body to cause the tissue to emit self-fluorescence. The excitation light has the predetermined wavelength that is filtered by the cut filter. The light emitting device is configured to emit light associated with the predetermined wavelength. The cut filter filters out excitation light and enables self-fluorescence light to be incident onto the image pickup device.

2 Claims, 4 Drawing Sheets

U.S. PATENT DOCUMENTS

| | | | |
|---|---|---|---|
| 4,884,133 A * | 11/1989 | Kanno et al. | 348/68 |
| 5,348,359 A * | 9/1994 | Boozer | 294/24 |
| 5,749,830 A * | 5/1998 | Kaneko et al. | 600/160 |
| 6,028,622 A * | 2/2000 | Suzuki | 348/65 |
| 6,110,106 A * | 8/2000 | MacKinnon et al. | 600/181 |
| 6,332,703 B1 * | 12/2001 | Tamaoki et al. | 362/551 |
| 6,422,994 B1 * | 7/2002 | Kaneko et al. | 600/160 |
| 6,471,636 B1 * | 10/2002 | Sano et al. | 600/109 |
| 6,680,844 B2 * | 1/2004 | Kim | 361/683 |
| 6,692,431 B2 * | 2/2004 | Kazakevich | 600/178 |
| 6,749,562 B2 * | 6/2004 | Nakamura et al. | 600/181 |
| 2001/0049473 A1 * | 12/2001 | Hayashi | 600/317 |
| 2002/0108610 A1 * | 8/2002 | Christopher | 128/200.26 |
| 2002/0188177 A1 * | 12/2002 | Miyanaga | 600/179 |
| 2002/0193664 A1 * | 12/2002 | Ross et al. | 600/178 |
| 2003/0035048 A1 * | 2/2003 | Shipp | 348/68 |
| 2003/0097122 A1 * | 5/2003 | Ganz et al. | 606/7 |
| 2003/0210543 A1 * | 11/2003 | Sharrah et al. | 362/187 |
| 2004/0032750 A1 * | 2/2004 | Watts et al. | 362/570 |

* cited by examiner

EXCITATION LIGHT ILLUMINATING PROBE, VIDEO ENDOSCOPE SYSTEM, AND VIDEO ENDOSCOPE FOR FLUORESCENCE OBSERVATION

BACKGROUND OF THE INVENTION

1. Field of the Invention

The invention relates to a video endoscope system for fluorescence observation which takes a subject image formed from self fluorescence radiating from a living body under the irradiation of excitation light, an illuminating probe for fluorescence observation for illuminating the subject with the excitation light, and a video endoscope for fluorescence observation. The present disclosure relates subject matter contained in Japanese Patent Application No. 2001-393815 (filed on Dec. 26, 2001), which is expressly incorporated herein by reference in its entirety.

2. Description of the Related Art

Conventionally, it is known that, when ultraviolet light (that is, excitation light) of certain wavelengths is incident on tissue of a living body, fluorescence (that is, self fluorescence) radiates at wavelengths longer than those of the incident excitation light, and that abnormal regions such as cancers and tumors emits self fluorescence of intensities lower than normal regions. Video endoscope systems for fluorescence observation using these phenomena take image of the intensity distribution of the self fluorescence with their image pickup devices and form monochrome images (that is, fluorescence images) which show bright and dark patterns indicating the distribution. Bright areas in the fluorescence images are likely to represent normal regions of the living body.

In a body cavity, hollows and recesses inaccessible to light (reference light and excitation light) emit no self fluorescence, forming dark areas in the fluorescence images. Hence, dark areas in fluorescence images do not necessarily represent abnormal regions. The video endoscope systems for fluorescence observation therefor compare the images (that is, normal images) of the body cavity wall taken under visible light (that is, reference light) with the fluorescence images to identify regions at which luminance ratio of the fluorescence images to the normal images fall short of a predetermined value. Because, such regions must be irradiated with the excitation light and are likely to be abnormal regions.

Figure 5:
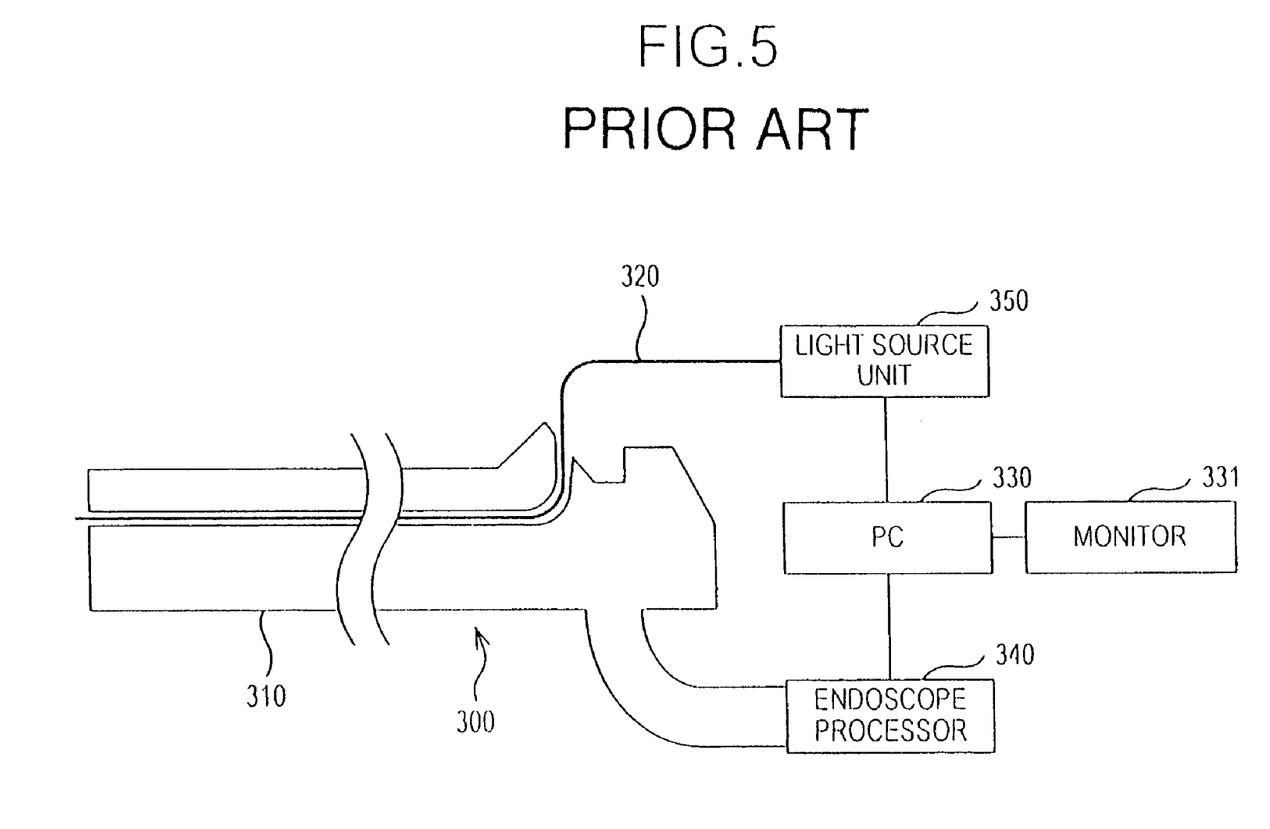
FIG. 5 is a schematic block diagram showing a conventional video endoscope system for fluorescence observation.

Hereinafter, a video endoscope system 300 for fluorescence observation having both the function of projecting excitation light and the function of projecting reference light will be described with reference to FIG. 5.

This video endoscope system 300 for fluorescence observation has a video endoscope 310, a fiber probe 320, a light source unit 350, an endoscope processor 340, a personal computer (hereinafter, abbreviated as PC) 330, and a monitor 331. The video endoscope 310 has an ordinary configuration and additionally has an excitation light cut filter arranged in front of its image pickup device. The fiber probe 320 can be inserted into and passed through a forceps channel which is built in and led through an insert part of the video endoscope 310. The light source unit 350 introduces excitation light and reference light to the fiber probe 320 alternately. The endoscope processor 340 processes image signals obtained by the image pickup device of the video endoscope 310 shooting a subject to generate image data frame by frame. The PC 330 synchronizes the generation of image data in the endoscope processor 340 with the switching of the excitation light and reference light in the light source unit 350. The PC 330 also compares image data under the irradiation of the excitation light and that under the irradiation of the reference light, both generated by the endoscope processor 340, and thereby generates image data that shows abnormal regions. The monitor 331 displays the image based on the image data generated by the PC 330.

The light source unit 350 must have at least an excitation light filter for transmitting the excitation light, a reference light filter for transmitting the reference light alone, a mechanism for switching optical paths from a single or two light sources to guide light to any one of the filters, and an optical system for coupling the optical paths having passed through the respective filters and introducing the resultant to the fiber probe 320. Accordingly, the light source device 350 inevitably becomes complicated in structure with an increase in size and weight. As a results there has been a problem of restrictions as to suitable examination sites and the like due to difficult transportation and layout.

Moreover, the optical fiber bundle in the fiber probe 320 is long and easy to break, in case it is made of grass fibers. If this optical fiber bundle is broken, the light from the light source unit 350 can no longer be transmitted to the extremity of the fiber probe 320, failing to illuminate the interior of the body cavity. On the other hand, the individual fibers in the optical fiber bundle are harder to break, in case they are made from plastic than the glass fibers. Such fibers, however, lack heat resistance.

Moreover, among the components of the light emitted from the light source(s), those other than the excitation light and reference light are cut off by the respective filters. Besides, the optical system for coupling the optical paths having passed through the respective filters (for example, a beam combiner) directs only components of the excitation light and reference light to the fiber probe 320, so that only a small fraction of the light emitted from the light source reaches the fiber probe 320. In addition, since the optical fiber bundle by no means achieves an internal transmittance of 100%, the emergent light is attenuated in light quantity as compared to the incident light. For that reason, subjects are often irradiated with insufficient quantity of light. Now, if the light source 351 is boosted in use to obtain sufficient quantity of irradiating light, the lamp life becomes short, causing higher medical costs, as well as the light source 351 generates a large amount of heat dangerously.

Another example of video endoscope systems for fluorescence observation is such that the excitation light and reference light are guided through a light guide fiber bundle which is originally arranged in the video endoscope as an illuminating optical system for normal observation. Even in this case, the light source unit must incorporate the mechanism for introducing the excitation light and reference light to the light guide fiber bundle selectively. This produces the same problems as described above.

SUMMARY OF THE INVENTION

The present invention devised to solve the foregoing problems provides an illuminating probe for fluorescence observation, which has a body made of a long flexible member, a tip member made from hard material and attached to a distal end of the body, a light emitting device arranged on the tip member to emit excitation light having such a wavelength as to excite tissue of a living body to emit self fluorescence, and a plurality of power supply lines connected to respective electrodes of the light emitting device and led through the entire length of the body.

The present invention also provides a video endoscope system for fluorescence observation includes a video emdoscope and an illuminating probe for fluorescence observation. The video endoscope has an insert part capable of being inserted into a body cavity, through which a forceps channel opening at its distal end is led, an objective optical system forming an image of a subject based on only a visible component of light emitting through the distal end of the insert part and then reflecting from a surface of the subject, and an image pickup device picking up an image of the subject formed by the objective optical system to output an image signal. The illuminating probe has a body made of a flexible member having an outside diameter smaller than the forceps channel and a length greater than the forceps channel, a tip member made from hard material attached to a distal end of the body, a light emitting device arranged on the tip member to emit excitation light having such a wavelength as to excite tissue of a living body in order to cause the tissue to emit self fluorescence, and a plurality of power supply lines connected to respective electrodes of the light emitting device, and led through the entire length of the body. The video endoscope system further includes a power supply unit for supplying the plurality of power supply lines of the illuminating probe with a drive current for making the light emitting device to emit the excitation light, a signal processing unit distinguishing and processing an image signal output in a period where the subject is irradiated with the excitation light, out of image signals successively output from the image pickup device and a display receiving an image signal processed by the signal processing unit to display an image based on the image signal.

The present invention also provides a video endoscope for fluorescence observation, which has an insert part capable of being inserted into a body cavity, a light emitting device arranged at a distal end of the insert part to emit excitation light having such a wavelength as to excite tissue of a living body to cause the tissue to emit self fluorescence, a plurality of power supply lines connected to respective electrodes of the light emitting device and led through entire length of the insert part, an objective optical system forming an image of a subject from only a visible component of light emitting through the distal end of the insert part and then reflecting from a surface of the subject, and an image pickup device picking up an image of the subject formed by the objective optical system to output an image signal.

According to the foregoing configurations, the light emitting device built in the tip member irradiates the subject with the excitation light while the tip member of the illuminating probe is opposed to the subject. Since the optical fibers having been used in conventional fiber probes are no longer needed, there will not occur the failure that a break in the optical fiber bundle in the fiber probe precludes the illumination inside the body cavity. The present invention is in no need of the conventional light source unit 350, either. This is combined with the absence of need for optical fibers to eliminate a loss of the illuminating light, and allow a large reduction in cost and the miniaturization of the system as well.

BRIEF DESCRIPTION OF DRAWINGS

The invention will be described below in detail with reference to the accompanying drawings, in which.

DESCRIPTION OF THE PREFERRED EMBODIMENTS

Hereinafter, embodiments of the video endoscope system according to the present invention will be described with reference to the drawings.

First Embodiment

Figure 1:
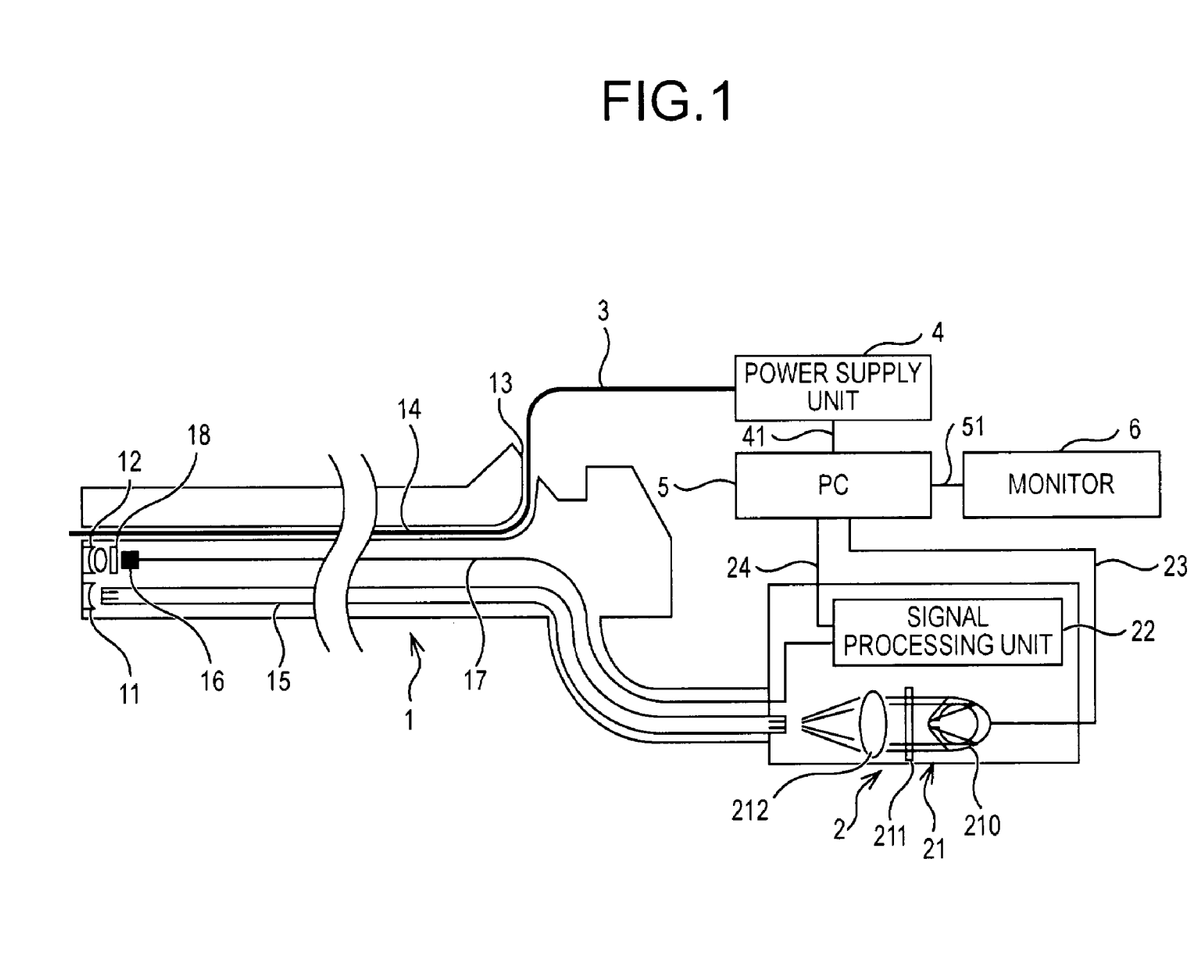
FIG. 1 is a schematic block diagram showing a video endoscope system for fluorescence observation which is a first embodiment of the present invention.

FIG. 1 is a schematic diagram showing the configuration of a video endoscope system which is a first embodiment of the present invention. This video endoscope system has a video endoscope 1, an endoscope processor unit 2, an illuminating probe for fluorescence observation (hereinafter, abbreviated as probe) 3, a power supply unit 4, a PC 5, and a monitor 6.

Although not shown specifically in FIG. 1, the video endoscope 1 has an insert part to be inserted into a living body and an operating part, which is connected to the proximal end of the insert part. The insert part is sectioned into a not-shown tip member which is made from hard material and a flexible tube whose distal end is sealed with the tip member. The tip member of this insert part is bored with at least three through holes. Among these through holes, two are fitted with a light distribution lens 11 and an objective lens 12 which are planoconcave lenses, respectively, with their flat faces facing outwards. The remaining one of the through holes connects to a forceps opening 13 made on the operating part, via a forceps channel 14 led through the flexible tube. Incidentally, a not-shown bending mechanism is built in an area of the insert part near the tip member. This bending mechanism is operated from a not-shown operating lever arranged on the operating part to bend the area.

The video endoscope 1 also incorporates a light guide 15. This light guide 15 is a fiber bundle consisting of a number of optical fibers bundled together. The light guide 15 is led through inside of the video endoscope 1 so that its distal end surface (projecting surface) is opposed to the light distribution lens 11 and its proximal end is led into a light source section 21 in the video endoscope processor unit 2.

Besides, an image pickup device 16 which is a charge-coupled device (CCD) area sensor is built in the tip member of the insert part of the video endoscope 1. The image pickup plane of this image pickup device 16 is located at a position where the objective lens 12 forms an image of a subject opposed to the distal end surface of the tip member of the video endoscope 1. The image pickup device 16 can photoelectrically convert the image of the subject into an image signal and output this image signal to a signal line 17. Note that an excitation light cut filter 18 for intercepting ultraviolet light and transmitting visible light is interposed to the optical path between the objective lens 12 and the image pickup device 16.

The video endoscope processor unit 2 contains the light source section 21 and a signal processing unit 22. The light source section 21 consists of a lamp 210, a rotary filter 211, and a condenser lens 212. The lamp 210 has a reflector in order to emit white light as parallel light. The rotary filter 211 rotates to sequentially insert a B filter for transmitting blue light, a G filter for transmitting green light, and an R filter for transmitting red light into the optical path of the white (W) light, one by one. Near the focus of the condenser lens 212 is arranged the proximal end face of the light guide 15. Through the use of the foregoing configuration, the light source section 21 makes blue light, green light, and red light incident on the proximal end face of the light guide 15, by turns, according to a control signal from the PC 5 to be described later. Then, these blue light, green light, and red light are guided through the light guide 15 and diffuse through the light distribution lens 11 to illuminate the subject opposed to the distal end surface of the tip member of the video endoscope 1. When the subject is sequentially illuminated with the blue light, green light, and red light, an image resulting from the blue light, an image resulting from the green light, and an image resulting from the red light are successively formed on the image pickup plane of the image pickup device 16. Then, this image pickup device 16 photoelectrically converts the subject images resulting from the blue light, green light, and red light into respective image signals (a B image signal under blue light irradiation, a G image signal under green light irradiation, and an R image signal under red light irradiation) as mentioned above, and sequentially outputs the same to the signal line 17. These light distribution lens 11, light guide 15, and light source section 21 correspond to the illuminating optical system.

The signal processing unit 22 processes the image signals output from the image pickup device 16 according to a frame sequential method, thereby synthesizing a color image signal. Specifically, while the light source section 21 is introducing the lights (blue light, green light, and red light) into the light guide 15, the signal processing unit 22 captures the B image signal, G image signal, and R image signal separately through the signal line 17 in succession, and synthesizes the captured image signals into a color image signal. The signal processing unit 22 internally retains the color image signal synthesized thus, and outputs it to the PC 5 as well. The signal processing unit 22 also has the function of synthesizing image signals for fluorescence observation when the light source section 21 does not introduce the lights (blue light, green light, and red light) into the light guide 15. This function will be further described after the description of the probe 3. Incidentally, when the light source section 21 does not introduce the lights (blue light, green light, and red light) into the light guide 15, the lamp 210 in the light source section 21 is turned off or a not-shown shutter in the light source section 21 shuts off the optical path between the condenser lens 212 and the light guide 15. The lamp 210 is switched on and off, or the shutter opens and closes the optical path, based on a control signal from the PC 5 to be described later.

Figure 2A:
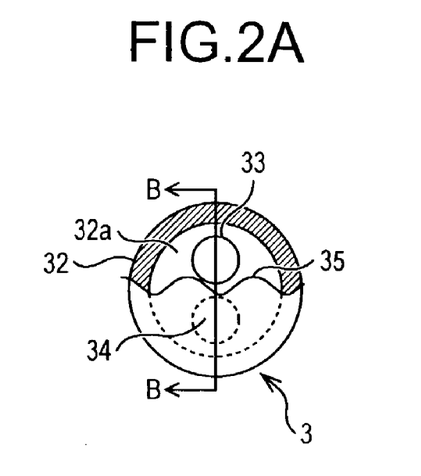
FIG. 2A is a front view of a probe in the first embodiment.
Figure 2B:
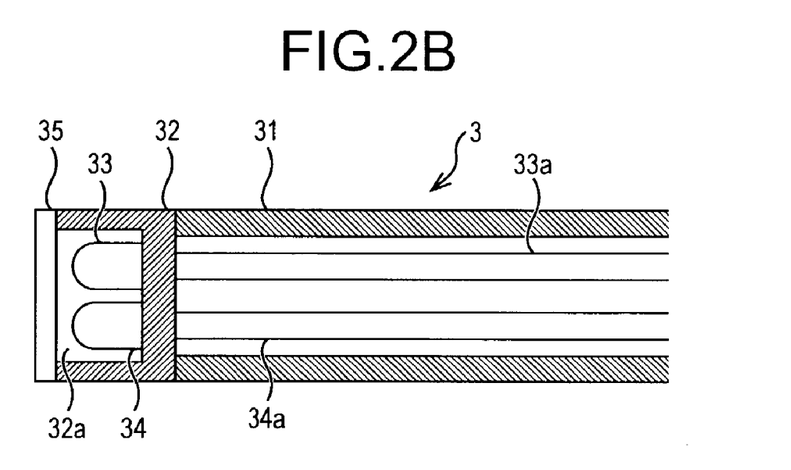
FIG. 2B is a longitudinal sectional view of the probe in the first embodiment.

Next, description will be given of the probe 3. FIG. 2A is a partially-sectioned front view of the distal end of the probe 3. FIG. 2B is a longitudinal sectional view taken along the line B—B of FIG. 2A. As shown in FIG. 2A and FIG. 2B, the probe 3 is assembled from a long tube 31 of generally cylindrical shape, a not-shown connector fixed to the proximal end of the tube 31, a cap 32 for sealing the distal end of the tube 31, a pair of light emitting devices 33 and 34 fixed to a bottom of a recess 32a formed on outer surface of the cap 32, leads 33a and 34a connected to the light emitting devices 33 and 34, respectively, and a lid 35 for sealing the recess 32a of the cap 32.

The tube 31 has an outside diameter smaller than the inside diameter of the above-described forceps channel 14. The tube 31 has a length greater than the sum of the length of the forceps channel 14 and the distance from the forceps opening 13 to a not-shown socket arranged on the power supply unit 4. The tube 31 is made of flexible elastic material (e.g., silicone). Consequently, when the insert part of the video endoscope 1 is inserted into a body cavity to bend the forceps channel 14, the probe 3 passed through this forceps channel 14 bends along this forceps channel 14. The probe 3, when pushed in from the forceps opening 13, can advance inside such a bent forceps channel 14.

The not-shown connector mentioned above is configured to be detachable/attachable from/to the not-shown socket arranged on the power supply unit 4. The end of this connector is provided with a plurality of electrodes which respectively conduct to a plurality of electrodes arranged in the not-shown socket of the power supply when the connector is connected to this socket.

The cap 32 is made from a transparent hard material in the shape of a closed-ended cylinder, having an outside diameter generally the same as that of the tube 31. The cap 32 seals the distal end of the tube 31 with its rear end.

One light emitting device 33 is a light emitting diode (LED) for emitting ultraviolet light in the range of 350–380 nm in wavelength, which can function as the excitation light to excite tissue of a living body of the subject. Among the examples available are NSHU550E (product name) from NICHIA CORPORATION, 260019 SERIES from MARL OPTOSOURCE, and UV750 (LED Chip Code) from LED TRONICS, INC.

The other light emitting device 34 is a conventional LED for emitting visible light functioning as reference light to illuminate the subject, which is, for example, an LED containing GaAs1-xPx. As the reference light the LED 34 emits red (R) light in the range of 580–670 nm in wavelength.

These LEDs 33 and 34 are fixed to inside the recess 32a of the cap 32 symmetrically about its center axis, with the directions of their respective light emissions in parallel to the center axis of the cap 32. In this connection, the peripheral wall of the foregoing cap 32 to surround the recess 32a is given such a height that the light beams diverging from these LEDs 33 and 34 will not be intercepted.

The leads 33a and 34a are two pairs of positive and negative power supply lines which establish conduction between the electrodes (positive and negative electrodes) of the LEDs 33, 34 and their corresponding electrodes built in the not-shown connectors. The leads 33a and 34a are led through the entire length of the tube 31, piercing through the proximal end of the cap 32. When the connector is connected to the socket of the power supply unit 4, the leads 33a and 34a supply drive currents from the power supply unit 4 to the LEDs 33 and 34, respectively.

The lid 35 has the shape of a disc having a diameter generally the same as the outside diameter of the cap 32. It is made of quartz glass which transmits both the excitation light and the reference light. The back surface of the lid 35 is bonded to the edge of the annular peripheral wall surrounding the recess 32a of the cap 32, so as to be fluid tight. This precludes the possibility that body fluids of the subject or antiseptic solutions may permeate into the recess 32a to contaminate the LEDs 33 and 34 when the probe 3 is cleaned after use. The LEDs 33 and 34 are also prevented from being damaged by external forces such as the impact when the probe 3 collides with a body cavity wall of the subject or the forceps channel 14, and the pressure of the antiseptic solutions.

The above-described tube 31, cap 32, and lid 35 have the same outside diameter, leaving no step from each other. On that account, the external surface of the probe 3 forms a generally smooth surface, which has neither gap nor corner entered and choked with a part of a body cavity wall or body fluid. This makes the external surface easy to clean and resistant to contaminations from bacteria and pathogens.

The power supply unit 4, as mentioned above, has the socket to which the connector fixed to the proximal end of the probe 3 is connected. The power supply unit 4 is also connected to the PC 5 via a signal line 41. When the not-shown connector of the probe 3 is connected to its socket, this power supply unit 4 supplies drive currents to the leads 33a and 34a alternately according to a control signal from the PC 5 to be described later, so that the LEDs 33 and 34 emit the excitation light and reference light alternately. As a result, the subject is irradiated with the excitation light and reference light alternately, provided that the distal end surface of the insert part of the video endoscope 1 is opposed to the subject and the probe 3 is inserted and passed through the forceps channel 14 until the front surface of its lid 35 protrudes from the through hole of the tip member of the insert part that leads to the forceps channel 14.

When the subject is irradiated with the excitation light, part of the light excites the subject to emit self fluorescence. The rest is reflected by the surface of the subject, that is, body cavity wall. The reflected excitation light and the emitted self fluorescence are incident on the objective lens 12. The excitation light cut filter 18 cuts off the excitation light component, so that only the self fluorescence reaches the image pickup device 16.

On the other hand, when the subject is irradiated with the reference light, part of the light is absorbed by the subject and the rest is reflected by the body cavity wall. This reflected reference light is incident on the objective lens 12 and reaches the image pickup device 16.

Consequently, when the subject is irradiated with the excitation light and reference light alternately, the image of the subject resulting from the self fluorescence and the image resulting from the reference light are successively formed on the image pickup plane of the image pickup device 16. Then, the image pickup device 16 photoelectrically convert the image resulting from the self fluorescence and the image resulting from the reference light into a fluorescence image signal and a reference image signal, respectively. These image signals are transferred to the signal processing unit 22 through the signal line 17 according to a control signal from the PC 5 to be described later. The objective lens 12 and excitation light cut filter 18 described above correspond to the objective optical system.

The signal processing unit 22 distinguishes the fluorescence image signal and reference image signal captured alternately, based on a control signal from the PC 5. The signal processing unit 22 retains the image signals inside, and determines the luminance ratios between these image signals pixel by pixel. The luminance ratio of each pixel is compared with a predetermined value (that is, threshold) and rendered binary value based on the result of the comparison. Thus, the signal processing unit generates a monochrome image signal (that is, image signal for fluorescence observation) which shows areas having luminance ratios lower than the threshold (that is, identified areas).

In accordance with a control signal from the PC 5 to be described later, the signal processing unit 22 also generates a diagnostic image signal based on the foregoing color image signal retained aside and the image signal for fluorescence observation, and outputs it to the PC 5. The diagnostic image signal is intended to display a diagnostic image in which the image showing the identified areas shown by the image signal for fluorescence observation is superimposed on a color image shown by the color image signal (that is, a pseudo color image showing the identified areas in blue).

The PC 5 outputs the control signals for controlling the light source section 21 and signal processing unit 22 in the video endoscope processor unit 2 and the power supply unit 4 through the signal lines 23, 24, and 41, respectively. Specifically, when an instruction to perform a normal observation (that is, observation of a body cavity wall under visible light) is given from not-shown input device, the PC 5 controls the light source section 21 in the video endoscope processor unit 2 to sequentially and repeatedly irradiate the subject with the blue light, green light, and red light. The PC 5 also makes the signal processing unit 22 repeatedly generate a color image signal in synchronization with the switching among the blue light, green light, and red light. The color image signal received from the signal processing unit 22 is output to the monitor 6. Now, if an instruction to perform a fluorescence observation (that is, observation of self fluorescence arising from a body cavity wall) is given from the not-shown input device, the PC 5 controls the light source section 21 of the video endoscope processor unit 2 and the power supply unit 4 to sequentially and repeatedly irradiate the subject with the blue light, green light, red light, excitation light, and reference light. The PC 5 also makes the signal processing unit 22 repeatedly generate a color image signal and an image signal for fluorescence observation alternately in synchronization with the switching among the blue light, green light, red light, excitation light, and reference light to generate the foregoing diagnostic image signal. The diagnostic image signal received from the signal processing unit 22 is output to the monitor 6. The input device may be a foot switch or a remote controller.

The monitor 6 may be a CRT (cathode-ray tube), a liquid crystal display, or a plasma display. The monitor 6, in a fluorescence observation, receives the diagnostic image signal from the PC 5 through a signal line 51 and displays the diagnostic image. In a normal observation, it receives the color image signal from the PC 5 through the signal line 51 and displays the color image. The monitor 6 corresponds to the display.

Second Embodiment

Hereinafter, description will be given of a video endoscope system for fluorescence observation, which is a second embodiment of the present invention. The second embodiment differs from the foregoing first embodiment only in the configuration of the probe and the operation of the power supply unit 4, PC 5, and video endoscope processor unit 2. The rest of the configuration is identical to the first embodiment. Thus, in the following description, the configuration common to the first embodiment will be omitted.

Figure 3A:
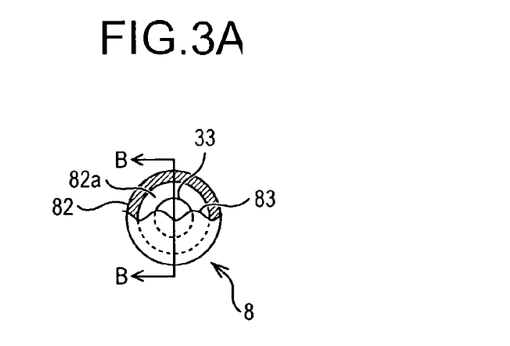
FIG. 3A is a front view of the probe in a second embodiment.
Figure 3B:
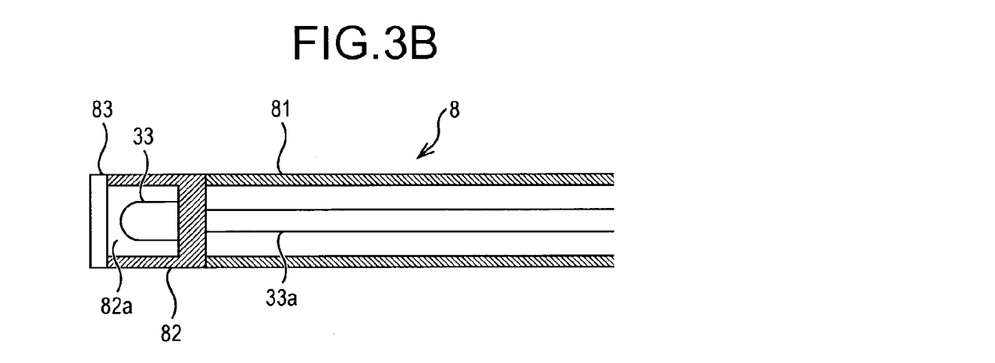
FIG. 3B is a longitudinal sectional view of the probe in the second embodiment.

FIG. 3A is a partially-sectioned front view of the distal end of a probe 8. FIG. 3B is a longitudinal sectional view taken along the line B—B of FIG. 3A. In FIG. 3A and FIG. 3B, the same reference numerals as in FIG. 2A and FIG. 2B are given to components identical to those of the probe 3 of the first embodiment. As shown in FIG. 3A and FIG. 3B, the probe 8 is assembled from a tube 81, a not-shown connector fixed to the proximal end of the tube 81, a cap 82 for sealing the distal end of the tube 81, an LED 33 fixed to a bottom of a recess 82a formed on outer surface of the cap 82, leads 33a connected to the LED 33, and a lid 83 for sealing the recess 82a of the cap 82. Note that the probe 8 has no component corresponding to the LED 34 and leads 34a for reference light which are arranged in the probe 3 of the first embodiment. The tube 81, cap 82, and lid 83 are thus smaller in outside diameter than the tube 31, cap 32, and lid 35 of the first embodiment, respectively. What pierce through the cap 82 are only the leads 33a. In other respects, the tube 81, cap 82, and lid 83 are configured the same as the tube 31, cap 32, and lid 35 in the probe 3 of the first embodiment, respectively.

In the second embodiment having the foregoing configuration, an image signal for fluorescence observation is generated in the following way. According to a control signal from the PC 5 to be described later, a subject is sequentially irradiated with red light from the light source section 21 in the video endoscope processor unit 2 and excitation light emitted from the LED 33 which is supplied with a drive current from the power supply unit 4 through the leads 33a. In other words, in the second embodiment, the red light from the light source section 21 in the video endoscope processor unit 2 is used as a substitute for the reference light which is emitted from the LED 34 in the first embodiment. Then, as in the first embodiment, the image of the subject resulting from self fluorescence and the image resulting from the red light are successively formed on the image pickup plane of the image pickup device 16. In accordance with a control signal from the PC 5 to be described later, the image pickup device 16 photoelectrically converts the image resulting from the self fluorescence and the image resulting from the red light and outputs the respective image signals to the signal processing unit 22 through the signal line 17. The signal processing unit 22 distinguishes the captured image signals based on a control signal from the PC 5, retains the image signals inside, and generates an image signal for fluorescence observation as in the first embodiment.

According to the second embodiment, when an instruction to perform a fluorescence observation is given from the not-shown input device, the PC 5 controls the light source section 21 in the video endoscope processor unit 2 and the power supply unit 4 to sequentially and repeatedly irradiate the subject with the blue light, green light, red light, and excitation light. The PC 5 also makes the signal processing unit 22 repeatedly generate a color image signal and an image signal for fluorescence observation alternately in synchronization with the switching among the blue light, green light, red light, and excitation light to generate a diagnostic image signal. The diagnostic image signal received from the signal processing unit 22 is output to the monitor 6.

Aside from the configuration described above, the second embodiment is identical to the first embodiment. Consequently, even in the present embodiment, the monitor 6 displays diagnostic images in fluorescence observations and color images in normal observations.

Third Embodiment

Hereinafter, description will be given of a video endoscope system for fluorescence observation which is a third embodiment of the present invention. The third embodiment differs from the foregoing second embodiment only in the configuration of the video endoscope 1 and in that the probe 8 is unnecessary. The rest of the configuration is identical to the second embodiment. Thus, in the following description, the configuration common to the foregoing second embodiment will be omitted.

Figure 4:
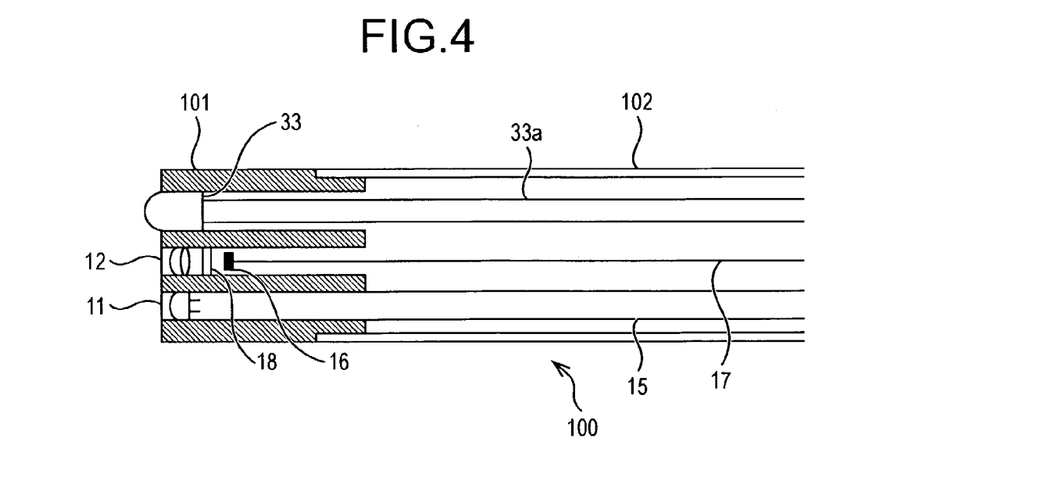
FIG. 4 is a longitudinal sectional view of the tip member of a video endoscope in a third embodiment.

FIG. 4 is a longitudinal sectional view of the distal end of an insert part of a video endoscope 100. Incidentally, in the third embodiment, the same reference numerals as in the foregoing first embodiment will be given to components identical to those of the first embodiment. Although not shown specifically in FIG. 4, the video endoscope 100 has the insert part to be inserted into a living body and an operating part, which is connected to the proximal end of the insert part. This insert part is sectioned into a tip member 101 which is made from hard material and a flexible tube 102 whose distal end is sealed with the tip member 101. A not-shown bending mechanism is built in an area of the flexible tube 102 near the tip member. The tip member 101 is bored with at least three through holes which extend in parallel to its center axis. Openings of these through holes at their outer side are fit with a light distribution lens 11, an objective lens 12, and an LED 33, respectively.

The LED 33 is fixed with the direction of its light emission in parallel to the center axis of the tip member 101. Its electrodes respectively conduct to a plurality of electrodes built in a not-shown connector arranged on the operating part of the video endoscope 100, through leads 33a which are led through inside of the insert part of the video endoscope 101.

The video endoscope 100 incorporates a light guide 15. Specifically, the light guide 15 is led through inside of the insert part of the video endoscope 100 with its distal end inserted into and fixed to the through hole of the tip member 101 that is fit with the light distribution lens 11. As in the first embodiment, the proximal end of the light guide 15 is led into the video endoscope processor unit 2.

An image pickup device 16 is fixed to the through hole that is fit with the objective lens 12 of the tip member 101. As in the first embodiment, the image pickup plane of this image pickup device 16 is located at a position where the objective lens 12 forms the image of a subject opposed to the distal end surface of the tip member 101. The image pickup device 16 can thus photoelectrically convert the image of the subject into an image signal and output this image signal to a signal line 17. Note that an excitation light cut filter 18 is arranged on the optical path between the objective lens 12 and the image pickup device 16.

According to the third embodiment described above, an image signal for fluorescence observation is generated in the following way. When an instruction to perform a fluorescence observation is given to the PC 5 from not-shown input device, the subject is sequentially irradiated with red light and excitation light. This red light is generated by the light source section 21 in the video endoscope processor unit 2 according to a control signal from the PC 5, guided through the light guide 15 and diverged through the light distribution lens 12 which is fit in the tip member of the video endoscope 100. The excitation light is emitted from the LED 33 which is supplied with a drive current from the power supply unit 4 through the leads 33a. In other words, in the third embodiment, the red light from the light source section 21 in the video endoscope processor unit 2 substitutes for the reference light as in the second embodiment.

Then, the image of the subject resulting from self fluorescence and the image resulting from the red light, each formed on the image pickup plane of the image pickup device 16, are photoelectrically converted into respective image signals. The image signals are transferred to the signal processing unit 22 according to a control signal from the PC 5. The signal processing unit 22 distinguishes these image signals individually, retains the image signals inside, and generates a fluorescence image signal and a diagnostic image signal as in the second embodiment.

Aside from the configuration described above, the third embodiment is identical to the first embodiment and second embodiment. Consequently, even in the third embodiment, the monitor 6 displays diagnostic images in fluorescence observations and color images in normal observations.

According to the present invention, it is possible to achieve a video endoscope system for fluorescence observation which is simple in structure, small and light, easy to transport and lay out, and thus free from restrictions as to the site of diagnosis, and is capable of contributing to suppressed medical costs.

I claim:

1. A video endoscope system for fluorescence observation comprising:

a video endoscope having an insert part configured to be inserted into a body cavity, a forceps channel having an opening provided at a distal end of the insert part, an objective optical system forming an image of a subject based on a visible component of light emitted through the distal end of said insert part, the visible component being reflected from a surface of the subject, a cut filter configured to filter out, from said light incident onto said objective optical system, a component of light having a predetermined wavelength, and an image pickup device picking up an image of the subject formed by said objective optical system to output an image signal;

an illuminating probe configured for fluorescence observation and having a flexible body member having an outside diameter smaller than said forceps channel and a length greater than said forceps channel, a tip member of a hard material attached to a distal end of said body member, said body being configured to extend through the forceps channel, a light emitting device positioned on said tip member to emit excitation light having a wavelength so as to excite tissue of a living body to cause the tissue to emit self fluorescence, the excitation light having the predetermined wavelength that is filtered by said cut filter, and a plurality of power supply lines connected to respective electrodes of said light emitting device and extending through a length of said body, said light emitting device being configured to emit light associated with said predetermined wavelength, said cut filter filtering out excitation light and enabling self fluorescense light to be incident onto said image pickup device;

a power supply unit for supplying said power supply lines of said illuminating probe with a drive current for causing said light emitting device to emit said excitation light;

a signal processing unit configured to distinguish an image signal output during a period when the subject is irradiated with said excitation light, from image signals successively output from said image pickup device, said signal processing unit being further configured to process said distinguished image signal; and a display that receives an image signal processed by said signal processing unit to display an image based on the image signal.

2. The video endoscope for fluorescence observation according to claim 1, wherein said light emitting device is a light emitting diode.

* * * * *